(12) United States Patent
Walker et al.

(10) Patent No.: US 7,255,709 B2
(45) Date of Patent: Aug. 14, 2007

(54) INTRAVASCULAR HEAT EXCHANGE CATHETER WITH TEMPERATURE SENSOR

(75) Inventors: Blair D. Walker, Mission Viejo, CA (US); Peter Barker, Bonsall, CA (US); Hortensia Pompa, San Clemente, CA (US); Xochitl Huezo, Lake Forest, CA (US); Lynn Miyeko Shimada, Orange, CA (US)

(73) Assignee: Alsius Corporation, Irvine, CA (US)

( * ) Notice: Subject to any disclaimer, the term of this patent is extended or adjusted under 35 U.S.C. 154(b) by 196 days.

(21) Appl. No.: 10/913,079

(22) Filed: Aug. 6, 2004

(65) Prior Publication Data

US 2005/0010273 A1   Jan. 13, 2005

Related U.S. Application Data

(60) Continuation-in-part of application No. 09/393,238, filed on Aug. 24, 2001, now Pat. No. 6,652,565, which is a division of application No. 09/376,524, filed on Aug. 18, 1999, now Pat. No. 6,419,643, which is a continuation-in-part of application No. 09/305,613, filed on May 5, 1999, now Pat. No. 6,368,304, which is a continuation-in-part of application No. 09/253,109, filed on Feb. 19, 1999, now abandoned, which is a continuation-in-part of application No. 09/063,984, filed on Apr. 21, 1998, now Pat. No. 6,126,684.

(60) Provisional application No. 60/492,818, filed on Aug. 6, 2003.

(51) Int. Cl.
*A61F 7/12* (2006.01)

(52) U.S. Cl. .................................... 607/105

(58) Field of Classification Search ............ 607/96, 607/104–106, 113
See application file for complete search history.

(56) References Cited

U.S. PATENT DOCUMENTS

| | | | |
|---|---|---|---|
| 4,796,640 A | 1/1989 | Webler | 128/736 |
| 5,271,410 A | 12/1993 | Wolzinger | 128/692 |
| 5,868,735 A * | 2/1999 | Lafontaine | 606/21 |
| 6,011,995 A * | 1/2000 | Guglielmi et al. | 607/99 |
| 6,497,721 B2* | 12/2002 | Ginsburg et al. | 607/106 |
| 6,514,249 B1* | 2/2003 | Maguire et al. | 606/41 |
| 6,540,771 B2* | 4/2003 | Dobak et al. | 607/105 |
| 6,547,788 B1* | 4/2003 | Maguire et al. | 606/41 |
| 6,620,188 B1* | 9/2003 | Ginsburg et al. | 607/106 |
| 6,679,906 B2 | 1/2004 | Hammack | 607/105 |
| 2004/0059235 A1* | 3/2004 | Saadat | 600/500 |

* cited by examiner

*Primary Examiner*—Roy D. Gibson
(74) *Attorney, Agent, or Firm*—John L. Rogitz

(57) ABSTRACT

An indwelling heat exchange catheter with integrated temperature sensor includes a catheter tube. A closed loop heat exchanger extends from the catheter tube. A temperature sensor can be integrally formed with the catheter tube such that it is insulated from the closed loop heat exchanger. The indwelling heat exchange catheter can further include a guide-wire tube that extends from the catheter tube and in such a case, the temperature sensor can be affixed to the guide-wire tube. Alternatively, a wire can extend through the catheter tube and the temperature sensor can be affixed to the wire.

11 Claims, 3 Drawing Sheets

INTRAVASCULAR HEAT EXCHANGE CATHETER WITH TEMPERATURE SENSOR

RELATED APPLICATIONS

This patent application claims priority from U.S. provisional application Ser. No. 60/492,818 filed on Aug. 6, 2003 and is a Continuation-in-Part of U.S. patent application Ser. No. 09/939,238, filed Aug. 24, 2001, now U.S. Pat. No. 6,652,565, which is a divisional of U.S. patent application Ser. No. 09/376,524, filed Aug. 18, 1999, now issued and assigned U.S. Pat. No. 6,419,643, which is a Continuation-in-Part of U.S. patent application Ser. No. 09/305,613, filed May 5, 1999, now issued U.S. Pat. No. 6,368,304, which is a Continuation-in-Part of U.S. patent application Ser. No. 09/253,109, filed Feb. 19, 1999, now abandoned, which was a Continuation-in-Part of U.S. patent application Ser. No. 09/063,984, filed on Apr. 21, 1998, now issued and assigned U.S. Pat. No. 6,126,684.

I. FIELD OF THE INVENTION

The present invention relates generally to methods and apparatus for exchanging heat with the body of a patient.

II. DESCRIPTION OF THE RELATED ART

Intravascular catheters have been introduced for controlling patient temperature. Typically, a coolant such as saline is circulated through an intravascular heat exchange catheter, which is positioned in the patient's bloodstream, to cool or heat the blood as appropriate for the patient's condition. The coolant is warmed or cooled by a computer-controlled heat exchanger that is external to the patient and that is in fluid communication with the catheter.

For example, intravascular heat exchange catheters can be used to combat potentially harmful fever in patients suffering from neurological and cardiac conditions such as stroke, subarachnoid hemorrhage, intracerebral hemorrhage, cardiac arrest, and acute myocardial infarction, or to induce therapeutic hypothermia in such patients. Further, such catheters can be used to rewarm patients after, e.g., cardiac surgery or for other reasons. Intravascular catheters afford advantages over external methods of cooling and warming, including more precise temperature control and more convenience on the part of medical personnel.

The following U.S. patents, all of which are incorporated herein by reference, disclose various intravascular catheters/systems/methods: U.S. Pat. Nos. 6,419,643, 6,416,533, 6,409,747, 6,405,080, 6,393,320, 6,368,304, 6,338,727, 6,299,599, 6,290,717, 6,287,326, 6,165,207, 6,149,670, 6,146,411, 6,126,684, 6,306,161, 6,264,679, 6,231,594, 6,149,676, 6,149,673, 6,110,168, 5,989,238, 5,879,329, 5,837,003, 6,383,210, 6,379,378, 6,364,899, 6,325,818, 6,312,452, 6,261,312, 6,254,626, 6,251,130, 6,251,129, 6,245,095, 6,238,428, 6,235,048, 6,231,595, 6,224,624, 6,149,677, 6,096,068, 6,042,559.

Regardless of the particular catheter used, it is clear that the temperature of the patient must be closely monitored. Systems have been provided to control the temperature of the heat exchange fluid that is circulated through a typical heat exchange catheter. These systems can use closed feedback from a temperature probe to monitor the temperature of the patient in which the heat exchange catheter is installed. For example, one or more temperature probes can be placed in a patient=s bladder, blood vessel, ear (tympanic), esophagus, or rectum. The present invention recognizes that the need for one or more temperature probes to monitor the temperature of a patient in which a heat exchange catheter is installed increases hospital costs due to the cost of the temperature probes and the personnel resources required to insert and maintain the probes in the patient.

As recognized herein, it is desirable to incorporate one or more temperature probes in the structure of a heat exchange catheter in order to monitor the temperature of a patient in which the heat exchange catheter is installed.

SUMMARY OF THE INVENTION

An indwelling heat exchange catheter includes a catheter tube and a closed loop heat exchanger that extends from the catheter tube. A temperature sensor can be integrally formed with the catheter tube such that the temperature sensor is insulated from the closed loop heat exchanger. Moreover, a guide-wire tube can extend from the catheter tube and the temperature sensor can be affixed to the guide-wire tube.

In a preferred embodiment, a wire can extend through the catheter tube and the temperature sensor can be affixed to the wire. Preferably, the wire is extended through the guide-wire tube. Further, the wire includes a curved end and the temperature sensor is affixed to the wire such that it is slightly spaced from the curved end of the wire. In a preferred embodiment, the temperature sensor can be a thermistor or a thermocouple.

In another aspect of the present invention, an indwelling heat exchange catheter includes a working tube and a closed loop heat exchanger. A heat exchange portion is established by the closed loop heat exchanger and the heat exchange portion is distanced from the working tube. In this aspect, a temperature sensor can be integrally formed with the working tube. When the heat exchange catheter is installed in a patient having blood, the blood flows between the heat exchange portion of the closed loop heat exchanger and the working tube.

In yet another aspect of the present invention, an indwelling heat exchange catheter includes means for exchanging heat with a patient=s blood and means for sensing temperature. In this aspect, the means for sensing temperature is insulated from the means for exchanging heat with the patient=s blood.

In still another aspect of the present invention, an indwelling heat exchange catheter includes a catheter tube and a guide wire tube that extends therefrom. A wire extends through the catheter tube and the guide-wire tube. Further, a temperature sensor is affixed to the wire.

The details of the present invention, both as to its construction and operation, can best be understood in reference to the accompanying drawings, in which like numerals refer to like parts, and which:

DETAILED DESCRIPTION OF THE PREFERRED EMBODIMENT

Figure 1:
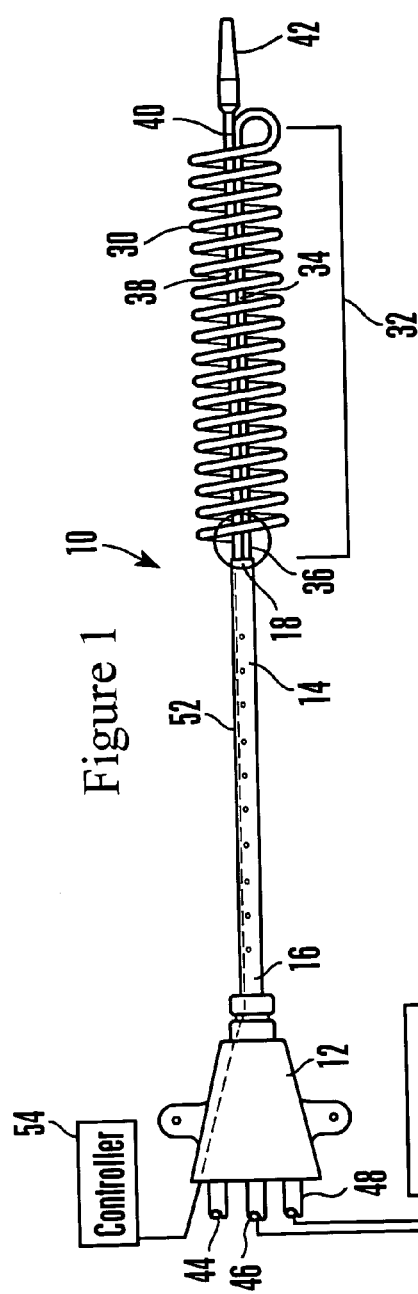
FIG. 1 is a plan view of a heat exchange catheter.
Figure 2:
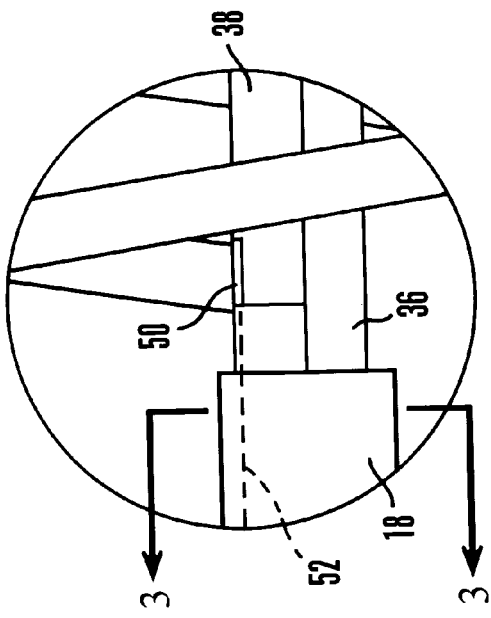
FIG. 2 is a detail view of the heat exchange catheter taken at circle 2 in FIG. 1.

Referring initially to FIG. 1, and the detailed view shown in FIG. 2, a heat exchange catheter is shown and is generally designated 10. As shown, the heat exchange catheter 10 includes a base 12 from which a preferably plastic catheter tube extends 14. The catheter tube 14 defines a proximal end 16 and a distal end 18. FIG. 1 shows that the proximal end 16 of the catheter tube 14 is connected to the base 12.

Figure 3:
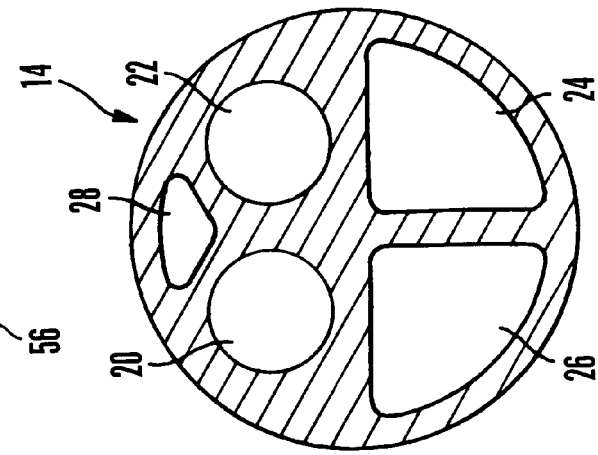
FIG. 3 is a cross-sectional view of the heat exchange catheter taken along line 3-3 in FIG. 2.

Referring briefly to FIG. 3, a cross section of the catheter tube 14 is shown. FIG. 3 shows that the catheter tube 14 is formed with a guide-wire lumen 20, an infusion fluid supply lumen 22, a heat exchange fluid supply lumen 24, and a heat exchange fluid return lumen 26. In a preferred embodiment, the catheter tube 14 can also be formed with a temperature sensor wire lumen 28.

Returning to FIG. 1, and the detailed view shown in FIG. 2, one or more working tubes can extend from the distal end 18 of the catheter tube 14. For example, a generally helix-shaped heat exchange balloon 30 can extend from the distal end of the catheter tube 14. As shown, the heat exchange balloon 30 can include coiled heat exchange portion 32 that is connected to a generally straight fluid return portion 34. It is to be understood that the heat exchange balloon 30 includes a first end (not shown) that is connected to the heat exchange fluid supply lumen 24 formed by the catheter tube 14 and a second end 36 that is connected to the heat exchange fluid return lumen 26 established by the catheter tube 14. As such, a closed loop heat exchanger is established and extends from the catheter tube 14.

FIG. 1 further shows a guide-wire tube 38 that extends from the catheter tube 14, e.g., from the guide-wire lumen 20 established within the catheter tube 14. As shown in FIG. 1, the guide-wire tube 38 defines a distal end 40 to which a guide tip 42 is attached. It can be appreciated that the guide tip 42 helps a user, e.g., a doctor or nurse, insert the catheter 10 into a patient=s vein or artery over a guide-wire (not shown). As shown, the guide-wire tube 38 and the return portion 34 of the heat exchange balloon 30 extend through the coiled portion 32 of the heat exchange balloon 30, i.e., centrally through the plural turns that comprise the coiled portion 32 of the heat exchange balloon 30.

FIG. 1 further shows an infusion fluid supply line 44 that extends from the base 12 of the catheter 10. The infusion fluid supply line 44 is in fluid communication with the infusion fluid lumen 22 established within the catheter tube 14. It is to be understood that the infusion fluid can carry medication, blood, or any other necessary fluid that needs to be injected into a patient.

As shown in FIG. 1, a heat exchange fluid supply line 46 and a heat exchange fluid return line 48 can extend from the base 12 of the catheter 10. In a preferred embodiment, the heat exchange fluid supply line 46 communicates with the heat exchange fluid supply lumen 24 established within the catheter tube 14. Further, the heat exchange fluid return line 48 can communicate with the heat exchange fluid return lumen 26 that is also established within the catheter tube 14.

Referring to FIG. 2, it is shown that the heat exchange catheter 10 further includes a temperature sensor 50 that, e.g., can be incorporated in the outer wall of the guide-wire tube 38, as described below. In a preferred embodiment, the temperature sensor 50 is a thermistor, but it can be appreciated that a thermocouple can be utilized instead. Moreover, it can be appreciated that more than one temperature sensor 50 can be incorporated into the heat exchange catheter 10, e.g., a second temperature sensor (not shown) can be placed near the distal end 40 of the guide-wire tube 38. FIGS. 1 and 2 further show a temperature sensor wire 52 that is connected to the temperature sensor 50. FIG. 1 shows that the temperature sensor wire 52 can connect the temperature sensor 50 to a controller 54.

As shown in FIGS. 1 and 2, and described in further detail below, the temperature sensor 50 is incorporated, e.g., into the outer wall of the guide-wire tube 38. The helix-shaped heat exchange balloon 30 winds around the guide-wire tube 38 and, as such, the heat exchange portion 32 of the heat exchange balloon 30 is distanced from the guide-wire tube 38 and the temperature sensor 50. As such, the heat transfer between the heat exchange fluid that flows through the heat exchange balloon 30 and the patients blood occurs at a location that is distanced from the temperature sensor 50. Any direct heating or cooling effects of the heat exchange fluid on the temperature sensor are minimized due to the distance between the temperature sensor and the heat exchange balloon 30.

Preferably, a heat exchange fluid, e.g., saline, flows from a source, e.g., a heat exchange bath 56, through the heat exchange fluid supply lumen 24 to the heat exchange balloon 30. Heat transfer occurs between the heat exchange fluid and a patient=s blood through the heat exchange balloon 30 along the coiled portion 32 of the heat exchange balloon 30. The heat exchange fluid can flow back through the return portion 34 of the heat exchange balloon 30 through the heat exchange fluid return lumen 26 back to the source, e.g., the heat exchange bath 56. During the heat exchange process, the temperature sensor 50 can be used to accurately monitor the patient=s temperature to ensure that the patient is not heated or cooled beyond a target temperature.

Figure 4:
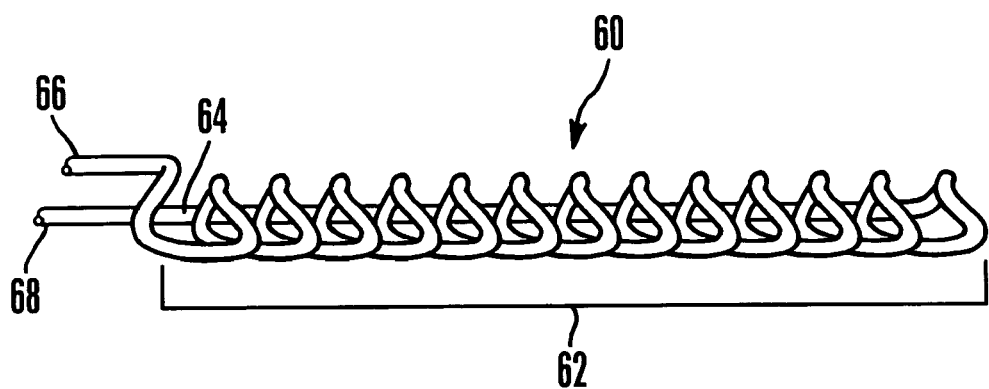
FIG. 4 is a perspective view of a first alternative heat exchange balloon.

Referring to FIG. 4, a first alternative embodiment of a heat exchange balloon is shown and is generally designated 60. As shown the heat exchange balloon 60 includes a generally serpentine-shaped heat exchange portion 62 and a generally straight fluid return portion 64. Moreover, the heat exchange balloon 60 defines a first end 66 and a second end 68. It is to be understood that the serpentine-shaped heat exchange balloon 60, shown in FIG. 4, can extend from the distal end 18 (FIG. 1) of the catheter tube 14 (FIG. 1). It is to be understood that the heat exchange balloon 60 can be connected to the catheter tube 14, e.g., by connecting the first end 66 of the heat exchange balloon 60 to the heat exchange fluid supply lumen 24 (FIG. 3) established within the catheter tube 14 and by connecting the second end 68 of the heat exchange balloon 60 to the heat exchange fluid return lumen 26 (FIG. 3) also established within the catheter tube 14. Thus, a closed loop heat exchanger is established and extends from the catheter tube 14. It can be appreciated that the guide-wire tube 38 shown in FIG. 1 can extend through the serpentine portion 62 of the heat exchange balloon 60.

Figure 5:
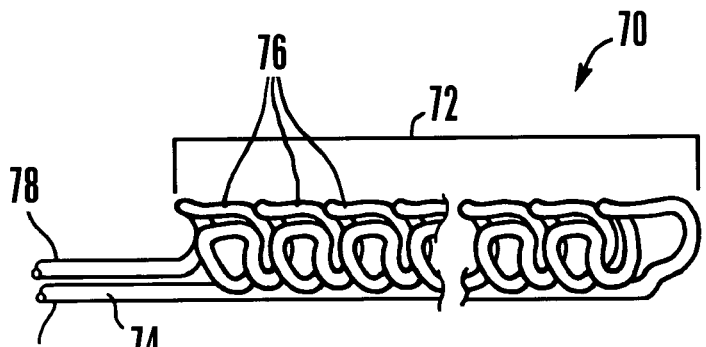
FIG. 5 is a perspective view of a second alternative heat exchange balloon.

FIG. 5 shows a second alternative embodiment of a heat exchange balloon that is generally designated 70. As shown, the heat exchange balloon 70 includes a heat exchange portion 72 and a generally straight fluid return portion 74.

FIG. 5 shows that the heat exchange portion 72 is comprised of plural links 76. Moreover, the heat exchange balloon 70 defines a first end 78 and a second end 80. It is to be understood that the heat exchange balloon 70, shown in FIG. 5, can extend from the distal end 18 (FIG. 1) of the catheter tube 14 (FIG. 1). It is to be understood that the heat exchange balloon 70 can be connected to the catheter tube 14, e.g., by connecting the first end 78 of the heat exchange balloon 70 to the heat exchange fluid supply lumen 24 (FIG. 3) established within the catheter tube 14 and by connecting the second end 80 of the heat exchange balloon 70 to the heat exchange fluid return lumen 26 (FIG. 3) also established within the catheter tube 14. Thus, a closed loop heat exchanger is established and extends from the catheter tube 14. It can be appreciated that the guide-wire tube 38 shown in FIG. 1 can extend through the heat exchange portion 72 of the heat exchange balloon 60.

Figure 6:
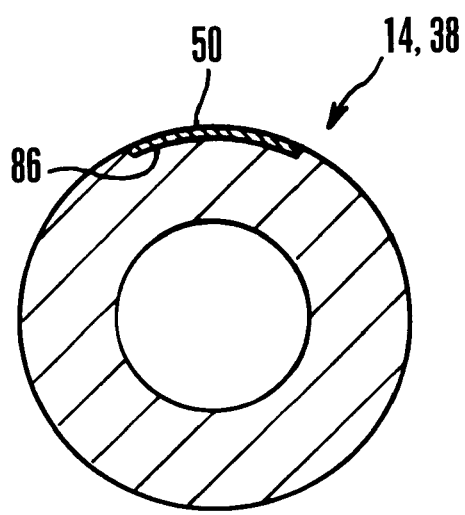
FIG. 6 is a cross-section view of a tube with a temperature sensor.
Figure 7:
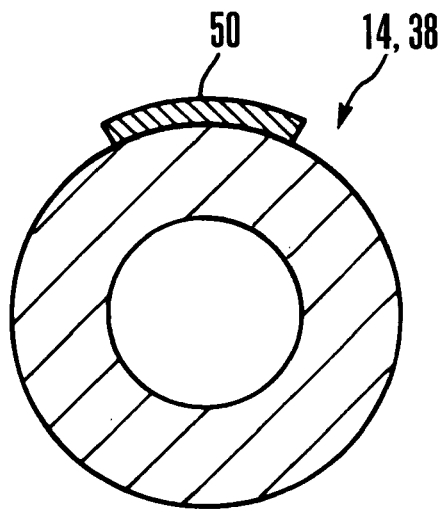
FIG. 7 is a cross-section view of an alternate tube with a temperature sensor.

FIG. 6, shows a cross-section of a tube, e.g., the guide-wire tube 38 or the catheter tube 14 shown in FIG. 1. As shown, the outer wall of the tube 14, 38 can be formed with a depression 86 into which the temperature sensor 50 (FIG. 2) can be installed. FIG. 7, on the other hand, shows that in an alternative embodiment, the temperature sensor 50 (FIG. 2) can be affixed directly to the outer surface of the tube 14, 38. In each of these embodiments, since the heat exchange portion 32, 62, 72 of the heat exchange balloon 30, 60, 70 is distanced from the guide-wire tube 38 and, hence, the temperature sensor 50, the blood flowing around the guide-wire tube 38 insulates the temperature sensor 50 from the direct heat transfer effects of the heat exchange fluid flowing through the heat exchange balloon 30, 60, 70.

Figure 8:
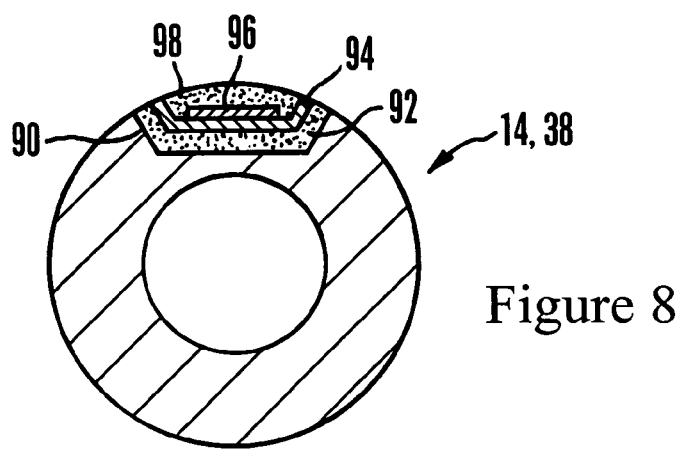
FIG. 8 is a cross-section view of a second alternate tube with a temperature sensor.

In yet another embodiment of the present invention, shown in FIG. 8, a tube, e.g., the guide-wire tube 38 or the catheter tube 14 shown in FIG. 1, is formed with a depression 90. It can be appreciated that the outer wall of the tube 14, 38 can be cut away to establish the depression 90. An insulating layer 92, e.g., cellular urethane, insulating foil, etc., can be deposited in the depression 90. Also, as shown, a non-porous layer 94, e.g., a piece of urethane balloon, can be affixed to the insulating layer 92. In this embodiment, a temperature sensor 96, can be affixed to the non-porous layer 94 and the temperature sensor 96 can be covered with a conductive layer 98, e.g., a conductive polymer adhesive.

It can be appreciated that the insulating layer 92 insulates the temperature sensor 96, e.g., from any heat transfer effects of the heat exchange fluid flowing through the catheter tube 14. Moreover, in the case in which cellular urethane is used for the insulating layer, the non-porous layer 94 prevents the insulating layer 92 from absorbing any of the conductive polymer adhesive used to establish the conductive layer 98.

Figure 9:
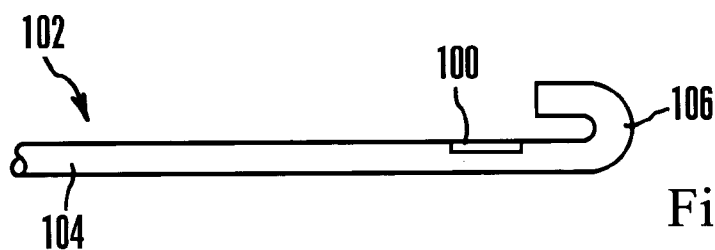
FIG. 9 is a plan view of a wire with a temperature sensor.

In still another embodiment of the present invention, shown in FIG. 9, a temperature sensor 100, e.g., a thermistor, can be incorporated into a wire 102 having a straight portion 104 and a curved portion 106. As shown in FIG. 9, the temperature sensor 100 is preferably incorporated into the wire 102 along the straight portion 104 of the wire 102 near the curved portion 106 of the wire 102. The wire 102 can be extended through the temperature sensor wire lumen 28 (FIG. 3) established within the catheter tube 14 or through the guide-wire tube 38 (FIG. 1).

Figure 10:
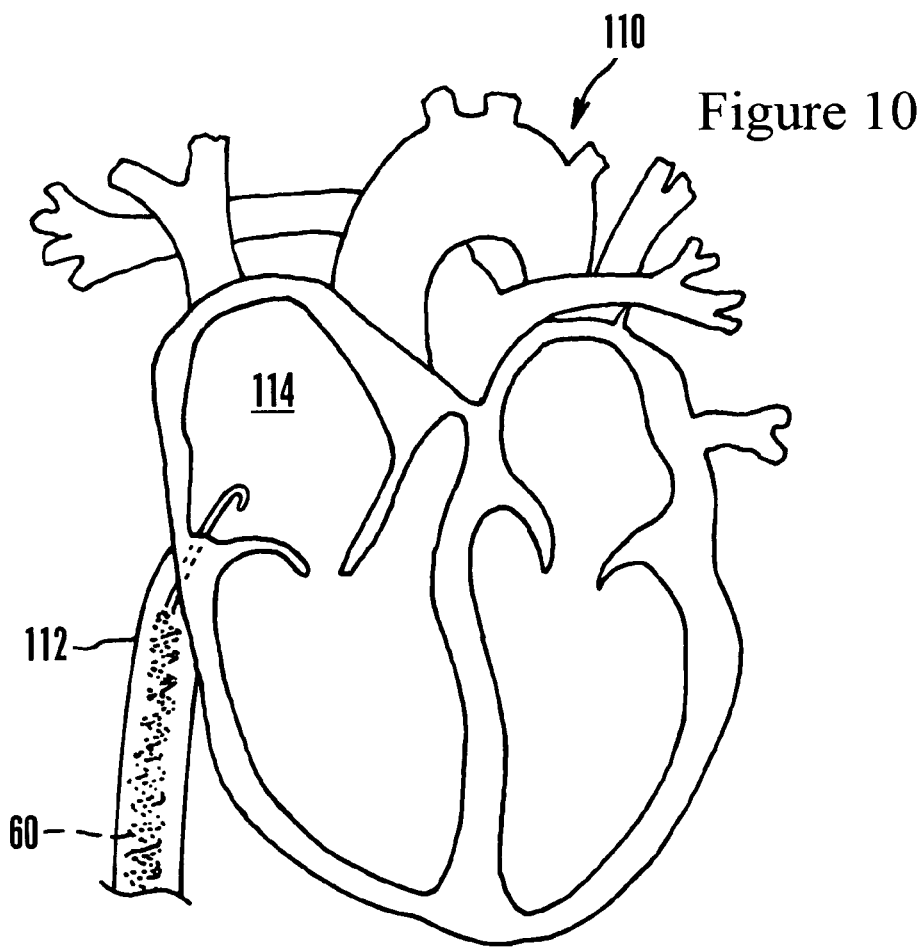
FIG. 10 is a plan view of a heart showing an intravascular heat exchange catheter inserted in the inferior vena cava.

FIG. 10 shows a heart 110 having an inferior vena cava 112 leading to a right atrium 114. As shown in FIG. 10, during use, the heat exchange balloon, e.g., the serpentine-shaped heat exchange balloon 60, can rest in the inferior vena cava 112 while the temperature sensor wire 102 can extend into the right atrium 114 of the patient=s heart 114. Accordingly, a patient=s temperature can be monitored directly from within his or her heart. This can be extremely useful when dealing with AMI/CA applications.

With the configuration of structure described above, the INTRAVASCULAR HEAT EXCHANGE CATHETER WITH TEMPERATURE SENSOR can be used to raise or lower the body temperature of a patient in which the catheter is installed. The temperature sensor 50 allows a user to closely monitor the temperature of the patient. Moreover, since the temperature sensor 50 is incorporated into the catheter the need for a separate temperature sensor is obviated.

While the particular INTRAVASCULAR HEAT EXCHANGE CATHETER WITH TEMPERATURE SENSOR as herein shown and described in detail is fully capable of attaining the above-described aspects of the invention, it is to be understood that it is the presently preferred embodiment of the present invention and thus, is representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it is to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. section 112, sixth paragraph, unless the element is expressly recited using the phrase "means for."

We claim:

1. An indwelling heat exchange catheter, comprising:
   at least one catheter tube;
   at least one closed loop heat exchanger extending from the catheter tube;
   at least one temperature sensor, the temperature sensor being thermally insulated from the closed loop heat exchanger, wherein the heat exchanger is configured for placement in a blood vessel while not blocking the vessel to allow blood to flow around the beat exchanger for facilitating heat exchange between the blood and the heat exchanger;
   at least one guide-wire tube extending from the catheter tube; and
   a wire extending through the catheter tube, the temperature sensor being affixed to the wire, wherein the wire comprises:
   a curved end curving back over an inner surface of a straight segment, the temperature sensor being affixed to the inner surface of the straight segment of the wire slightly spaced from the curved end of the wire such that the sensor is disposed in the bloodstream without touching a wall of the blood vessel when positioned in a body.

2. The catheter of claim 1, wherein the wire is extended through the guide-wire tube.

3. The catheter of claim 1, wherein the temperature sensor is one of the following: a thermistor or a thermocouple.

4. An indwelling heat exchange catheter, comprising:
   at least one catheter tube;
   at least one closed loop heat exchanger extending from the catheter tube; and
   at least one temperature sensor, the temperature sensor being thermally insulated from the closed loop heat exchanger, wherein the heat exchanger is configured for placement in a blood vessel while not blocking the vessel to allow blood to flow around the heat exchanger for facilitating heat exchange between the blood and the heat exchanger;
   at least one guide-wire tube extending from the catheter tube, the temperature sensor being affixed to the guide-wire tube, wherein the guide-wire tube establishes a depression in which the temperature sensor is installed and wherein an insulating layer is disposed within the depression, the temperature sensor being affixed to the insulating layer and wherein an electrically conductive layer is disposed over the temperature sensor.

5. The catheter of claim 4, further comprising:
   a non-porous layer disposed within the depression between the insulating layer and the temperature sensor.

6. An indwelling heat exchange catheter, comprising:
   at least one working tube;
   at least one closed loop heat exchanger;
   at least one heat exchange portion established by the closed loop heat exchanger, the heat exchange portion being distanced from the working tube;
   at least one temperature sensor;
   at least one guide-wire tube, the temperature sensor being affixed to an outer wall of the guide-wire tube; and
   wherein when the heat exchange catheter is installed in a patient having blood, the blood flows between the beat exchange portion of the closed loop heat exchanger and the working tube, an electrically conductive layer being disposed over the temperature sensor.

7. The catheter of claim 6, wherein the temperature sensor is one of the following: a thermistor or a thermocouple.

8. The catheter of claim 6, wherein the guide-wire tube establishes a depression in which the temperature sensor is installed.

9. The catheter of claim 8, further comprising:
   an insulating layer disposed within the depression, the temperature sensor being affixed to the insulating layer.

10. The catheter of claim 6, further comprising:
    a non-porous layer disposed within the depression between the insulating layer and the temperature sensor.

11. An indwelling heat exchange catheter, comprising:
    at least one working tube;
    at least one closed loop heat exchanger,
    at least one heat exchange portion established by the closed loop heat exchanger, the heat exchange portion being distanced from the working tube;
    at least one temperature sensor;
    at least one guide-wire tube; and
    wherein when the heat exchange catheter is installed in a patient having blood, the blood flows between the heat exchange portion of the closed loop heat exchanger and the working tube, the temperature sensor being affixed to a wire extending at least partially through the catheter, wherein the wire comprises:
    a curved end segment, the temperature sensor being affixed to the wire slightly spaced from the curved end segment of the wire on a straight portion of the wire facing a portion of the curved end segment.

* * * * *